Figure 1:
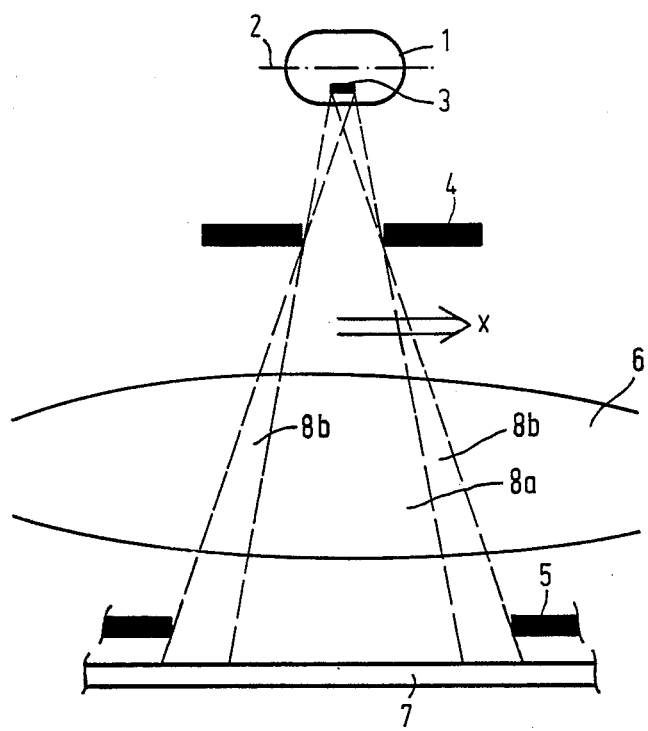

United States Patent [19]

Frings et al.

[11] Patent Number: 4,894,850
[45] Date of Patent: Jan. 16, 1990

[54] X-RAY APPARATUS FOR SLIT RADIOGRAPHY

[75] Inventors: Gottfried Frings, Stolberg; Walter Hillen; Ulrich Schiebel, both of Aachen, all of Fed. Rep. of Germany

[73] Assignee: U.S. Philips Corporation, New York, N.Y.

[21] Appl. No.: 236,585

[22] Filed: Aug. 25, 1988

[30] Foreign Application Priority Data

Aug. 29, 1987 [DE] Fed. Rep. of Germany ....... 3728878

[51] Int. Cl.⁴ ............................................. G21K 5/10
[52] U.S. Cl. ..................................... 378/62; 378/125; 378/146; 378/147
[58] Field of Search ............... 378/145, 146, 147, 125, 378/144, 55, 62, 14

[56] References Cited

U.S. PATENT DOCUMENTS

| | | | |
|---|---|---|---|
| 4,096,389 | 6/1978 | Ashe et al. | 378/147 |
| 4,773,087 | 9/1988 | Plewes | 378/146 |

Primary Examiner—Carolyn E. Fields
Assistant Examiner—David P. Porta
Attorney, Agent, or Firm—Jack E. Haken

[57] ABSTRACT

The invention relates to the elimination of streak-like artefacts in slit radiography which are caused by an axial excursion of the rotary anode X-ray tube used for making the radiographs. These streaks can be eliminated by adapting the speed of displacement of the X-ray beam, the number of revolutions per unit time of the anode and the intensity profile of the radiation beam to one another so that for each point the intensity modulation in the half-shade area, caused by the periodic displacement of the focal point, is compensated for.

5 Claims, 2 Drawing Sheets

X-RAY APPARATUS FOR SLIT RADIOGRAPHY

The invention relates to an X-ray apparatus, comprising a rotary-anode X-ray tube and a diaphragm device for forming a radiation beam from the X-rays produced by the X-ray tube, the radiation beam and a recording medium exposed thereto being displaced relative to one another in one direction during an X-ray exposure.

X-ray apparatus of this kind are known, i.e. apparatus using a flat recording medium (see German Patent Document OS 23 51 473) as well as with cylindrical recording medium (German Patent Document OS 35 34 768). In comparison with a conventional X-ray apparatus in which the recording medium is simultaneously exposed at all areas, a substantially improved scattered radiation suppression is thus obtained. On the other hand, the X-ray tube load is substantially higher, because the part of the X-rays which is used for imaging is substantially smaller than in conventional X-ray apparatus. In order to prevent unacceptably along exposure times, a rotary anode X-ray tube must be used in such X-ray apparatus. When the rotary anode X-ray tube is mounted so that its rotary axis extends parallel to the displacement direction of the X-ray beam, anode discs having a very small anode angle can be used, which anode discs offer, for the same (apparent) focal spot size a higher radiation intensity than rotary anode X-ray tubes having a larger anode angle.

However, it has been found that in such a case, and in any other case where the axis of the X-ray tube does not extend exactly perpendicularly to the displacement direction, streaks which extend perpendicularly to the displacement direction can occur in the radiograph, even when the focal spot of the X-ray tube and the diaphragm device are exactly adjusted and displacement takes place at an exactly uniform speed.

It is an object of the present invention to construct an X-ray apparatus of the kind set forth so that the described streak-like artefacts are substantially suppressed in the radiograph. This object is achieved in accordance with the invention in that the intensity profile of the radiation beam at the area of the recording medium, the speed of the relative displacement between the radiation beam and the recording medium, and the number of revolutions per unit time of the rotary anode X-ray tube are adapted to one another during the exposure so that the intensity fluctuations caused by periodic shifts of the focal spot during the exposure compensate for one another.

The invention is based on the recognition of the fact that the streak-like artefacts in the radiograph are due to a periodic movement of the focal spot of the X-ray tube in the axial direction. These motions, caused notably by an unavoidable axial excursion of the anode disc, represent an oscillation having the frequency of the rotary anode drive and comprise a component in the displacement direction of the radiation beam when the axis of rotation of the anode disc does not extend exactly perpendicularly to the displacement direction.

Despite their low amplitude, due to these oscillations, being superposed on the linear displacement motion taking place at a constant speed, points on the recording medium which succeed one another in the displacement direction are exposed to the half-shade range of the X-rays for a different period of time, which half-shade is caused by the stopping of the X-ray beam in conjunction with the finite magnitude of the focal spot. This results in a location-dependent intensity modulation of the X-rays, which in its turn causes the described streaks.

Obviously, the intensity modulation and the resultant streaks can be suppressed when the secondary diaphragm associated with the diaphragm device and situated between the examination zone and the recording medium narrows the X-ray beam having passed through the examination zone so that the half shade ranges, also referred to hereinafter as "edges", are cut off. However, part of the radiation intensity which has passed through the examination zone and having loaded the patient (if a patient to be examined is arranged therein) will also be lost for imaging.

The invention follows a different approach where the radiation of the half shade-range or the edges of the intensity profile can also be used. The invention is based on the recognition of the fact that for a predetermined intensity profile the speed and the number of revolutions per unit time can be chosen so that for an arbitrary point on the recording medium, during the passage through the edges of the intensity profile one phase in which the intensity is increased because of the oscillation (in comparison with the case without oscillations) is opposed by another phase in which the intensity is reduced to the same extent, so that the fluctuations compensate one another over the entire path of the point through the edges of the intensity profile.

Such a compensation can be achieved in various ways:

A first possibility consists in that the adaptation is such that the time during which a point on the recording medium is passed by an edge of the intensity profile corresponds to the reciprocal value of the number of revolutions per unit time of the rotary anode X-ray tube or to an integer multiple thereof.

Another possibility consists in that the time during which a point on the recording medium is passed by an edge plus the plateau of the intensity profile corresponds to the reciprocal value of the number of revolutions per unit time of the rotary anode X-ray tube or to an integer multiple thereof.

In a preferred embodiment in accordance with the invention, the intensity profile is shaped so that the length $(x3-x2)$ of the plateau relates to the length $(x2-x1)$ of an edge or to the length $(x3-x1)$ of an edge plus the plateau as $m/s$ or $n/s$, respectively, where s is an integer and m and n are integers corresponding to the number of revolutions of the rotary anode during the passage of a point on the recording medium through an edge or through an edge plus the plateau, respectively, of the intensity profile.

This preferred embodiment enables both above requirements to be simultaneously satisfied, resulting in a pronounced minimum of the intensity modulation as a function of the frequency (for a predetermined displacement speed and a predetermined intensity profile). The shape of the intensity profile can be adapted to the requirements by way of the position and the aperture of the (primary or secondary) diaphragms of the diaphragm device.

Figure 2:
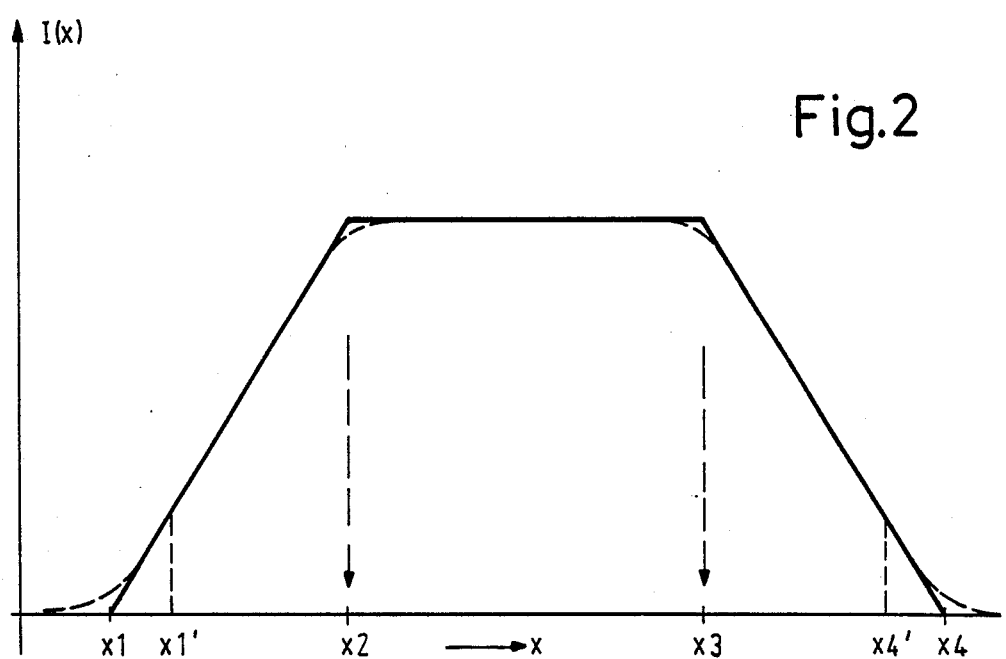
Figure 3:
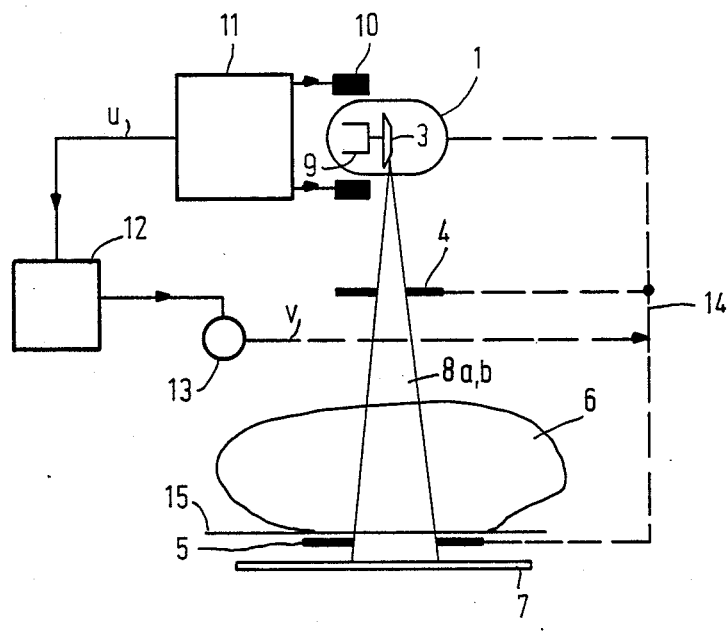

The invention will be described in detail hereinafter with reference to the drawings. Therein:

FIG. 1 diagrammatically shows an X-ray apparatus of the kind set forth (not to scale);

FIG. 2 shows a typical intensity profile for the X-ray beam generated in such an X-ray apparatus, and FIG. 3 shows an X-ray apparatus in accordance with the invention.

The reference numeral 1 in FIG. 1 denotes an X-ray tube which is only diagrammatically shown. The anode disc (not shown) of this rotary anode X-ray tube is rotatable about a horizontal axis 2. The reference numeral 3 denotes the apparent focal spot of the rotary anode X-ray tube (the actual focal spot is inclined in accordance with the anode angle of the anode disc). A diaphragm device forms an X-ray beam from the X-rays generated in the focal spot 3. The diaphragm device consists of a primary diaphragm 4 which is situated between the focal spot and the examination zone (contrary to the drawing, usually in the direct vicinity of the focal spot) and of a secondary diaphragm 5 which is situated between the examination zone, symbolized by the object 6 to be examined, and the recording medium 7. The diaphragms 4 and 5 are symmetrically arranged with respect to the focal spot 3 so that the X-ray beam extends symmetrically with respect to the perpendicular from the centre of the focal spot to the record carrier 7. For the recording medium use can be made of a film but also of a photoconductor which converts the X-rays into a charge pattern, or of a storage phosphor, for example in accordance with U.S. Pat. No. 4 239 968.

Because the focal spot 3 of the X-ray tube 1 is not exactly point-shaped, but rather has a finite extension, the radiation beam formed by the primary diaphragm 4 comprises an area 8a in which all X-rays passing through the primary radiation diaphragm 4 are present on both sides of this area there exists a half shade range 8b in which only a part of the X-rays passing through the primary diaphragm 4, is present.

The primary diaphragm 4 and the secondary diaphragm 5 have an aperture such that the format of the recording medium 7 is fully covered by the X-rays in the direction perpendicular to the plane of drawing of FIG. 1, whilst in the direction perpendicular thereto and parallel to the direcion of the axis of rotation 2 only a comparatively small part of the recording medium is covered. In order to obtain a complete X-ray exposure, therefore, the X-ray beam 8a, 8b and the examination zone 6 must be displaced relative to one another in the direction of the arrow X, i.e. parallel to the axis of rotation 2; in the case of a recording medium 7 having a cylindrically curved surface, this medium must additionally be rotated so that the X-rays having passed through a given point of the examination zone are always incident on the same point on the recording medium. The drives required for this purpose have been omitted in FIG. 1 for the sake of clarity.

The solid lines in FIG. 2 represent the variation of the X-ray intensity I at the area of the recording medium 7 as a function of the location x. This variation represents the intensity profile of the X-ray beam in the displacement direction. The intensity profile is trapezidal when the intensity of the emitted X-rays is the same throughout the focal spot. The horizontal part between the limits x2 and x3 corresponds to the area 8a and the edges between x1 and x2 as well as between x3 and x4 correspond to the half-shade areas 8b.

Said periodically reciprocating movement of the focal spot 3 in the direction of the axis of rotation 2, becoming hardly larger than a few tens of μm in practice, causing "jittering" of the edges of the intensity profile so that a point on the recording medium -hich passes through these edges is exposed more or less than a point in the case of a fixed focal spot. This intensity modulation Im is a function of the x coordinate of the relevant point. It can be demonstrated that for this point:

$$Im = c(\cos(wt1+\beta) - \cos(wt2+\beta) + \cos(wt3+\ominus) - \cos(wt4+\beta)). \quad (1)$$

Therein:
  w is the circular frequency of the anode disc, i.e. its number of revolutions per unit time multiplied by the factor $2\pi$,
  c is a constant,
  $\beta$ is a phase angle which depends only on the x coordinate of the relevant point, and
  t1 ... t4 are the instants at which the relevant point reaches the locations x1 ... x4 in the intensity profile.

The intensity modulation can be suppressed in a number of ways:

(A) the intensity modulation Im becomes zero when:
$$x2 - x1 = x4 - x3 = mv/u \quad (2)$$

Therein:
  m is an integer,
  v is the speed at which the X-ray beam is displaced relative to the examination zone, and
  u is the number of revolutions per unit time of the anode disc of the rotary-anode X-ray tube 1.

The equation (2) demonstrates that the time during which a point on the recording medium passes through an edge (i.e. the path x1−x2 or the path x3−x4) must be m times longer than the duration of one revolution of the anode disc.

In this case the focal spot has completed exactly one (or more) periods of its reciprocating motion during the period of time in which a point passes through one of the edges (for example t2−t1), so that the intensity fluctuations caused thereby, being superimposed during the intensity increase or decrease during the passage through an edge, compensate for one another.

(B) The intensity modulation, and hence the streak-like artefacts in the radiograph, are suppressed when:

$$x3 - x1 = x4 - x2 = nv/u \quad (3)$$

where n is an integer. This equation demonstrates that the time required for passing through an edge (i.e. for example, the path x1−x2) plus the plateau x2−x3 of the intensity profile corresponds to the duration of one revolution or to a multiple thereof.

In this case a point passes through the ascending edge (x1, x2) of the intensity profile in the same phase position of the anode oscillation as the descending edge. As a result, during the passage through an edge each point receives an amount of radiation intensity less (more) which is equal to that received more (less) during the passage through the other edge.

Particularly attractive circumstances are obtained when the two equations (2) and (3) are simultaneously satisfied. Around the zero point of the intensity modulation as a function of the number of revolutions a particularly wide minimum is then obtained, so that substantially no streak-like artefacts occur, not even when the values of the number of revolutions per unit time u or the displacement speed v are not maintained strictly in accordance with the equation (2) or (3).

The conditions of the equations (2) and (3) are simultaneously satisfied if, in addition to the equation (2) or the equation (3) the equation (4) is satisfied.

$$x3 - x2 = sv/u \qquad (4)$$

where s is an integer. This additional condition implies that the time during which the plateau x3−x2 passes across a point on the recording medium corresponds to the reciprocal value of the number of revolutions per unit time or to a multiple thereof.

The conditions according to one of the equations (2) or (3) can be satisfied for any arbitrary intensity profile by a suitable choice of the displacement speed v and/or the number of revolutions per unit time u of the anode. However, if the equation (4) is also to be satisfied, the variation of the intensity profile must be such that the length x3−x2 of the plateau and the length (x1−x2 or x3−x4) of an edge relate as two integer numbers.

The intensity profile can be adapted to the requirements in various ways. For example, the primary diaphragm can be readjusted or its distance from the X-ray source 1 can be changed; the simplest possibility, however, consists in the readjustment of the secondary diaphragm 5 so that a part of the half shade region 8b is cut off. In that case the intensity profile reaches the value zero already at the locations x1' or x4' (see FIG. 2), so that these values must be inserted into the equations (2), (3) and (4) instead of x1 and x4.

In practice the X-ray intensity is not distributed uniformly across the focal point 3; it usually decreases in the direction of the edges of the focal spot. Consequently, the intensity profile will not have the shape denoted by solid lines in FIG. 2, but rather a shape where the differential quotient of the intensity I along the path x varies continuously as a function of the path x. This means that at the area of x1, x2, x3 and x4 the intensity profile is rounded as denoted by broken lines in FIG. 2. In this case, however, the edge is also formed by the solid straight line which represents the tangent to the intensity variation at approximately half the maximum intensity. In this case the points x1, x2 etc. are again defined by the points of intersection between this tangent and the plateau or the straight line I(x)=0.

For the suppression of the streak-like artefacts in the radiograph the following procedure can be used in practice: for a given X-ray source and a fixed geometry of the recording system (aperture of the primary diaphragm and the secondary diaphragm as well as their distance from the focal spot), the intensity profile is measured (or calculated) once in order to determine the positions x1, x2, x3 and x4, x1 and x4 possible being replaced by x1' and x4'. The equations (2) and (3) are then satisfied in that either, for a predetermined displacement speed v, the number of revolutions per time unit u of the anode or, for a predetermined number of revolutions per unit time u, the displacement speed v is controlled in accordance with the equation (2) or (3). However, in the case of a predetermined number of revolutions per unit time and a predetermined displacement speed it is alternatively possible to change the aperture of the primary diaphragm and/or the secondary diaphragm. However, when the dimension of the secondary diaphragm is greater than that of the X-ray beam, the values X1 and X4 must be inserted in the equations (2) and (3).

FIG. 3 diagrammatically shows an X-ray apparatus in accordance with the invention. On the inclined annular surface of the anode disc 3 there is situated a focal spot for the X-rays; the anode disc is connected to a rotor 9 which is driven by a stator 10. The drive energy is supplied by a controllable generator 11. Moreover, the generator 11 detects, on the basis of the currents and in the manner described in German Patent Document PS 27 32 862, the reaching of a given number of revolutions; this event is signalled to a control circuit 12 which acts on a motor 13. The motor 13 acts on a mechanical coupling device (only diagrammatically denoted by strokes) between the primary diaphragm 4 and the secondary diaphragm 5 and preferably also on the X-ray source 1, so that they are displaced in the horizontal direction and the radiation beam 8a, 8b is displaced across the recording medium and hence different areas of the patient 6 positioned on a table top 15 are irradiated.

An X-ray exposure is then made as follows. First the generator 11 is activated so that the anode disc 3 is accelerated. When the predetermined number of revolutions per unit time u is reached, the drive is either switched off completely or is switched over to a lower energy which suffices exactly to sustain the desired number of revolutions per unit time u. Subsequently, the control circuit 12 for the motor 13 is activated so that the coupling device 14 is displaced, and hence also the radiation beam 8a, 8b, until the desired speed v, indicated by the control circuit 12, is reached after a defined displacement. At that instant the high voltage is switched on in the high voltage generator (not shown) for the X-ray tube 1, so that the X-ray tube generates X-rays wherefrom the radiation beam 8a, 8b is formed. The X-rays are switched off as soon as, after a period of time which depends on the speed v and the length of the recording medium 7, the recording medium 7 has been completely exposed.

Evidently, prior to the start of the exposure the unit 14 must be positioned so that the edge of the recording medium is reached only after completion of the path within which the nominal speed v is reached or when the high voltage is switched on.

For a predetermined speed v it is also possible to control the number of revolutions per unit time of the anode so that the equation (2) and/or (3) is satisfied. To this end, the generator 11 must form part of a control circuit in which the number of revolutions per unit time of the anode disc 3 is continuously measured and the energy is varied until the reference value u of the number of revolutions per unit time is reached.

In an X-ray apparatus as described in DE-OS 35 34 768 in which the recording medium 7 is not flat but cylindrical and rotates about the cylinder axis, the number of revolutions per unit time of the recording medium rotates the cylinder axis must be synchronized with the displacement speed of the cylinder, so that the displacement speed corresponds to the speed on the drum surface.

In the X-ray apparatus the length (x3−x2) of the plateau amounts to, for example 6 mm. The primary diaphragm 4 is adjusted so that a base width (x4−x1) of the radiation profile amounting to 14 mm would occur if it were not restricted 12 mm (x4'−x1') to by the aperture of the secondary diaphragm 5. For this intensity profile and a relative displacement speed v of 450 mm/s between the radiation beam 8a, 8b and the recording medium 7, 50 or 100 (3); however, a number of 150 revolutions per second is to be preferred, because the equations (2) and (3) are then simultaneously satisfied and the intensity minimum is so wide that small deviations from the exact values according to the equations (2) or (3) will not cause appreciable streaks in the radiograph.

What is claimed is:

1. An X-ray apparatus comprising:

an x-ray tube which includes a rotating anode;

diaphragm means for forming an X-ray radiation beam from X-rays produced at a focal spot on the anode;

X-ray recording means disposed in the beam;

means which effect a relative movement of the recording means with respect to the beam during an X-ray exposure of the recording means; and synchronizing means which adjust the rate of rotation of the anode and/or the relative speed of said beam with respect to the recording means as a function of an intensity profile of the beam at the recording means to compensate the exposure of the recording means for fluctuations in the intensity of the beam which are caused by periodic movement of the focal spot.

2. The apparatus of claim 1 wherein the diaphragm means produces a beam which has a substantially trapezoidal intensity profile at the recording means and the synchronizing means adjust the rate of rotation and/or relative speed so that an edge of the profile passes over a point on the recording means during an integral number m of rotations of the anode.

3. The apparatus of claim 2 wherein the diaphragm means produces a beam which has a ratio of plateau length to edge length of m/s, where s is an integer.

4. The apparatus of claim 1 or 2 wherein the diaphragm means produces a beam which has a substantially trapezoidal intensity profile at the recording means and the synchronizing means adjust the rate of rotation and/or relative speed so that the plateau and one edge of the profile passes over a point on the recording means during an integral number n of rotations of the anode.

5. The apparatus of claim 4 wherein the diaphragm means produces a beam which has a ratio of plateau length to edge length plus plateau length of n/s, where s is an integer.

* * * * *